(12) United States Patent  
Busch et al.

(10) Patent No.: US 6,304,781 B1
(45) Date of Patent: Oct. 16, 2001

(54) ELECTROSTIMULATOR

(75) Inventors: Ulrich Busch; Klaus Bartels, both of Berlin (DE)

(73) Assignee: Biotronik Mess- und Therapiegeräte GmbH & Co. Ingenieurbüero Berlin, Berlin (DE)

(*) Notice: Subject to any disclaimer, the term of this patent is extended or adjusted under 35 U.S.C. 154(b) by 0 days.

(21) Appl. No.: 09/182,419

(22) Filed: Oct. 30, 1998

(30) Foreign Application Priority Data

Oct. 31, 1997 (DE) .............................................. 197 49 710

(51) Int. Cl.[7] ........................................................ A61N 1/37
(52) U.S. Cl. ................................................... 607/28; 607/8
(58) Field of Search ........................................ 607/7, 8, 28

(56) References Cited

U.S. PATENT DOCUMENTS

| 4,245,643 | * | 1/1981 | Benzing, III et al. ................. 607/28 |
| 4,613,850 | | 9/1986 | Timmermann . |
| 5,282,840 | * | 2/1994 | Hudrlik ................................. 607/28 |
| 5,436,566 | | 7/1995 | Thompson et al. . |
| 6,016,445 | * | 1/2000 | Baura ....................................... 607/8 |

FOREIGN PATENT DOCUMENTS

| 0 057 944 | 8/1982 | (EP) . |
| WO 98 19738 | 5/1998 | (WO) . |
| WO 99 58192 | 11/1999 | (WO) . |

* cited by examiner

*Primary Examiner*—George R. Evanisko
(74) *Attorney, Agent, or Firm*—Venable; George H. Spencer; Robert Kinberg

(57) ABSTRACT

Electrostimulator (2), comprising an interface for connecting a working electrode (2), as well as a pulse generator that is connected on the output side to the interface for transmitting electrical pulses to the working electrode (10), with a first measuring instrument (10) that is connected to the interface for measuring the electrical voltage present at the interface and/or the electrical current flowing over the interface, as well as an arithmetic unit, connected on the input side to the first measuring instrument, for computing an output signal reflecting the capacity of the working electrode in dependence on the current and/or voltage at the interface.

20 Claims, 4 Drawing Sheets

ELECTROSTIMULATOR

BACKGROUND OF THE INVENTION

The invention relates to an electrostimulator having an output connection to a working electrode and a test generator having an output connected to the output connection for generating either a pulse-shaped or periodically changeable test signal and feeding the signal to the output connection.

Implantable pacemakers have been used for some time to treat cardiac disfunctions, as is known, and in particular bradycardia conditions. These pacemakers transmit electrical stimulation pulses to the heart via an endocardially arranged stimulation electrode if the heart stops beating or does not beat sufficiently fast.

Owing to the fact that each stimulation pulse leads to a partial discharge of the pacemaker battery, efforts are made to lower the amplitude of the stimulation pulses as much as possible to increase the battery service life, wherein it should be taken into consideration that the heart will no longer react with a contraction to a stimulation with an amplitude below a specified threshold value, also referred to as stimulus threshold value.

It is therefore also known to conduct a so-called stimulus threshold value test to determine the stimulus threshold value of the heart individually for each pacemaker carrier and to be able to program the stimulation pulse amplitude accordingly. For this, the pacemaker emits successive stimulation pulses with a decreasing amplitude, wherein it is respectively determined whether the heart reacts with a contraction to the preceding stimulation pulse by evaluating an extracorporeal recorded electrocardiogram (ECG). The stimulus threshold value for the heart in that case approximates the amplitude at which the heart is barely stimulated by the stimulation pulse.

However, one problem with this is that a change in the stimulus threshold value, e.g. due to changes in the chronic stimulus threshold, is not detected during the normal pacemaker operation, which can lead either to a stimulation with unnecessarily high amplitudes or—considerably worse—to an unsuccessful stimulation.

That is why in recent years pacemakers have become known which determine automatically whether the heart is successfully stimulated by a stimulation pulse and which accordingly optimize the amplitude for the stimulation pulses. For this, the pacemaker measures the so-called evoked potential by means of the pacemaker electrode, in each case immediately following a stimulation pulse, which evoked potential causes the cardiac muscle contraction and represents the response to the preceding stimulation pulse. The problem is that the electrode system which encloses two metal electrolytic boundary surfaces is electrically charged with a stimulation pulse, owing to its capacitive properties, so that the evoked potentials can be concealed by the electrical after-effects of a stimulation pulse (artifacts on both boundary layer capacities). For that reason, this concept is only used in connection with high-capacity electrodes which, owing to their high capacity, are charged only to a relatively low voltage by a stimulation pulse, which does not interfere with the detection of the evoked potential.

Until now, suitable electrodes were selected on the basis of an extracorporeal measurement of the electrode capacity by means of separate measuring instruments, resulting in higher implantation expenditure and the disadvantage that a post-operative change in the electrode capacity is not detected by the pacemaker. Problems furthermore had to be expected with the new implantation of a pacemaker and continued use of the previously implanted electrode.

SUMMARY OF THE INVENTION

Thus, it is the object of an invention to create an electrostimulator, which permits measuring the electrode capacity even in the implanted state, without using separate instruments.

Starting with an electrostimulator as defined in the preamble to claim 1, this object is solved by its characterizing features.

The above and other objects are accomplished according to the invention by the provision of an electrostimulator comprising: an output connection for connection to a working electrode; a test generator having an output connected to the output connection for generating one of a pulse-shaped and periodically changeable test signal and feeding the test signal to the output connection; a first measuring device having an input connected to the output connection for measuring at least one of an electrical voltage present at the output connection and a current flowing over the output connection; and an evaluation device having an input connected at least indirectly to the first measuring device for generating an output signal that reflects the working electrode capacity in dependence on at least one of the current and voltage present at the output connection.

One variant of the invention provides that the pulse generator generates a pulse with a specified electrical charge Q for determining the electrode capacity, e.g. a constant-current pulse with specified amplitude and duration. Subsequently, the voltage U to which the stimulation electrode was charged by the pulse is measured by the measuring instrument at the output connection between pacemaker and stimulation electrode, and this measured value is transmitted to a subsequently connected arithmetic unit, which uses the following formula:

$$\frac{1}{C_{EL}} + \frac{1}{C_{CASE}} = \frac{U}{Q},$$

to compute the electrode capacity $C_{EL}$ while the housing capacity $C_{CASE}$ is known. However, the invention is not limited to a constant-current pulse for this variant. The important thing is that the electrical charge Q that is discharged with the pulse or the current flowing during the pulse duration is known. It is optionally possible to generate a pulse with specified charge for this, or to measure the time during which a pulse with known current course is discharged. A constant-current pulse is preferably used.

In order to improve the accuracy of the capacity measurement, resulting from a reduction in polarization effects at the electrode system, the constant-current pulse can be a double pulse, with mutually inverse current direction of the two partial pulses.

Another variant of the invention provides that a pulse with specified voltage course, preferably a constant voltage pulse, be transmitted to determine the electrode capacity.

If the stimulation electrode is viewed electrically as a series connection, consisting of a capacity $C_{E1}$ and an ohmic resistor $R_{E1}$, then the voltage over the electrode capacity increases exponentially during the pulse duration for a constant voltage pulse and approaches asymptotically the voltage amplitude $U_{Stim}$ of the pulse. In accordance with the formula:

$$C_{El} = \frac{-T}{R \cdot \ln\left(1 - \frac{U_{EL}}{U_{Stim}}\right)}$$

the electrode capacity $C_{E1}$ is then computed from the pulse duration T, the voltage amplitude $U_{Stim}$ of the pulse, the electrode voltage $U_{E1}$ measured at the output connection following the end of the pulse, as well as the ohmic charging resistance R, consisting of the ohmic resistance $R_{E1}$ for the electrode and additional ohmic resistances in the charging circuit, which are presumed to be known.

According to another variant of the invention, the pacemaker electrode is a component of an oscillating circuit, wherein the electrode capacity can be determined based on the effect it has on the oscillatory response of the oscillating circuit. The pacemaker for this variant has an internal inductance that is connected to the output connection or can be connected to it via a switching element. In this case, the inductance can be either connected in series or parallel with the electrode capacity. The oscillating circuit set up in this way is stimulated by an oscillator, which is also optionally connected to the interface or can be connected to it via a switching element.

The oscillator for one embodiment of this variant generates a preferably sinusoidal oscillating signal with constant frequency and voltage amplitude, so that the current flowing through the oscillating circuit depends on the frequency tuning between the oscillator on the one hand and the oscillating circuit on the other hand. Thus, measuring the current flowing over the interface makes it possible to compute the electrode capacity from the oscillator frequency and the inductance of the oscillating circuit.

In contrast, another embodiment of this variant provides that the oscillating frequency of the oscillating circuit with phase-limit capacity be determined by changing the frequency of the oscillator while simultaneously measuring the current, thereby making it easy to calculate the electrode capacity according to the Thomson oscillation formula.

Measuring the impedance spectrogram of the electrode system with a continuous oscillator represents another variant. In that case, the course of the electrode impedance is recorded in dependence on the signal frequency by impressing a variable frequency constant-current signal or a constant-voltage signal and measuring the voltage or current at the electrode system. The Helmholtz capacity and also the electrolytic resistance and the Faraday resistance can be computed from the spectrum.

BRIEF DESCRIPTION OF THE DRAWINGS

Other advantageous modifications of the invention will become apparent from the following detailed description when considered with the aid of the figures and, wherein.

DETAILED DESCRIPTION OF THE INVENTION

Figure 1:
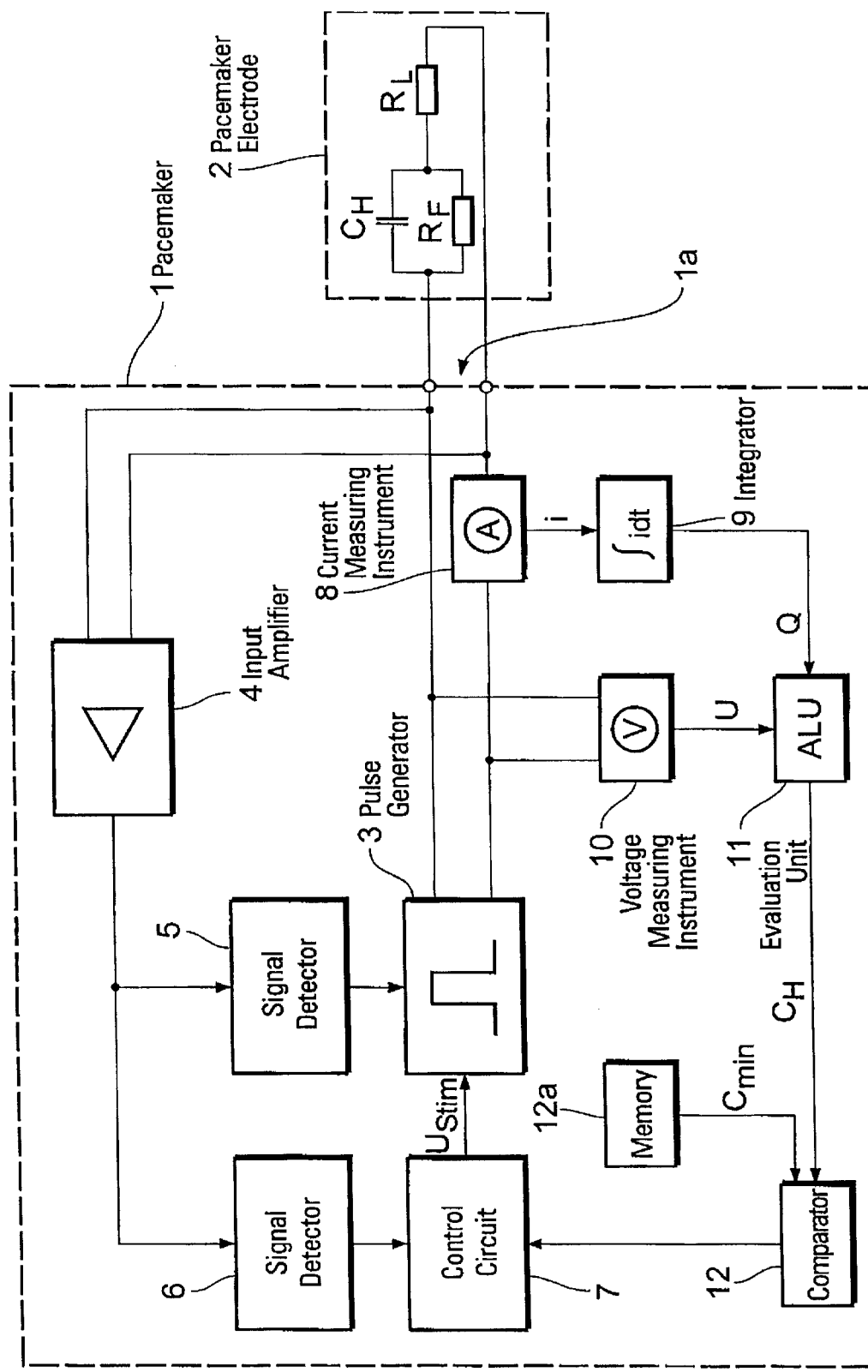
FIG. 1 Shows as the preferred embodiment of the invention a pacemaker with stimulation electrode in the form of an operational block diagram.

The pacemaker 1, shown as a block diagram in FIG. 1, makes it possible to transmit stimulation or pacemaker pulses to the heart via a stimulation electrode 2, which is shown here in the equivalent circuit diagram. In order to simplify, only one of the electrode/electrolytic boundary surfaces of the electrode system is shown here in the equivalent circuit diagram.

The equivalent circuit diagram for the pacemaker electrode 2 which is to be arranged endocardially is intended to reflect the essential electrical characteristics of the metal/tissue boundary layer at the pacemaker electrode. Thus, a so-called Helmholtz double layer forms at the boundary between the pacemaker electrode 2 and the surrounding tissue (not shown here), which is simulated through a parallel connection of a capacitor $C_H$ and an ohmic resistance $R_F$. It must be taken into consideration here that the ohmic resistance $R_F$ of the Helmholtz double layer depends strongly on the electrode potential. The pacemaker electrode 2 furthermore has an ohmic line resistance $R_L$ that is connected in series with the above-described impedance of the Helmholtz double layer, as well as—to be precise—an electrolytic resistance (important with small electrode surfaces) in series thereto, which is not shown separately here.

On the one hand, the pacemaker electrode 2 permits the transmission of stimulation pulses to the heart. The stimulation pulses in this case are generated in the traditional way with the pulse generator 3, shown in detail in FIG. 2, which has on the output side an output connection la for connecting the pacemaker electrode 2.

On the other hand, the pacemaker electrode 2 functions to detect the electrical heart activity caused by spontaneous, i,e not stimulated, cardiac actions, so that the transmission of a stimulation pulse can be blocked, if necessary. For one thing, this allows maintaining the natural heart rhythm as much as possible. For another thing, an unnecessary stimulation is avoided in this way, which contributes to extending the service life of the pacemaker 1 battery. The pacemaker 1 has an input amplifier 4 for this, which amplifies the electrical heart signals, picked up via the pacemaker electrode 2, and transmits these to a signal detector 5 for detection of spontaneous cardiac actions. If the signal detector 5 identifies a spontaneous cardiac action, it transmits a blocking signal to the pulse generator 3, which subsequently resets its internal time clock and stops the transmitting of a stimulation pulse.

The stimulation electrode 2 furthermore makes it possible to detect the cardiac response which, in the end, permits the adaptation of the stimulation pulse intensity to the individual stimulus threshold value of the pacemaker carrier.

In simple terms, a successful heart stimulation presupposes that the amplitude time integral of the individual stimulation pulses exceeds the individual stimulus threshold value, so that the heart reacts to a stimulation pulse with a contraction. (Strictly speaking, the chronaxy-rheobase correlation, known to the person skilled in the art, must be observed.) On the one hand, it is desirable to lower the amplitude time integral of the stimulation pulses as much as possible in order to save energy in the interest of extending the service life of the battery. It, however must be ensured that the stimulation pulses are sufficiently strong to excite the heart. After each stimulation pulse, the pacemaker 1 therefore checks the electrical heart signals picked up via the pacemaker electrode 2 and determines whether evoked potentials occur that represent a response to the immediately preceding stimulation pulse. The output signal for input amplifier 4 is therefore transmitted to a special signal detector 6 to detect evoked potentials.

The stimulation pulse intensity is adjusted via a control circuit 7, connected on the input side with the signal detector 6, which slowly lowers the stimulation voltage $U_{Stim}$ as long as the heart is stimulated and increases the stimulation voltage in stages, if a heart-muscle contraction is not detected following a stimulation pulse.

Figure 2:
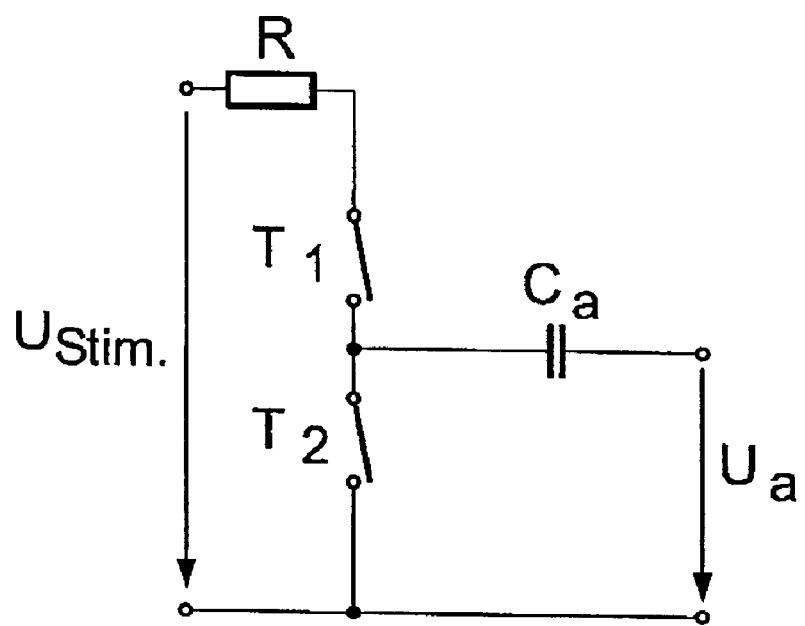
FIG. 2 Shows the pulse generator for the pacemaker shown in FIG. 1, as a simplified circuit diagram.

In order to produce a stimulation pulse, the transistor $T_1$, shown in FIG. 2, is closed by a control electronic that is not shown here, whereas transistor $T_2$ is opened. Since the output capacitor $C_a$ is completely discharged at the start of a stimulation pulse, the full voltage $U_{Stim}$ is initially present at the interface. However, over the duration of the stimulation pulse, the output capacitor $C_a$ is charged by the current flowing over the interface, which leads to an exponential decrease of the voltage present at the interface, respectively during one pulse. Making the simplified assumption of a purely ohmic charge, the output capacitor $C_a$ thus limits the maximum charge discharged during one stimulation pulse to the value required for charging the output capacitor $C_a$ to the full voltage $U_{Stim}$.

Therefore, the output capacitor $C_a$ as well as the Helmholtz capacity $C_H$ of the electrode pair are fully charged immediately following each stimulation pulse.

For one thing, the maximum stimulation voltage that can be reached with the next stimulation pulse is reduced by the output capacitor voltage $Uc_a$, so that no new pulse with the full voltage can be generated immediately following a stimulation pulse.

For another thing, the charging of the electrode capacity $C_H$ interferes with the measuring of the natural cardiac activity since the voltage of the electrode capacity $C_H$ is superimposed on the electrical heart signals.

Following the end of a stimulation pulse, the transistor $T_2$ is therefore closed, whereas the transistor $T_1$, is opened, so that the output capacitor $C_a$ and the electrode capacity $C_H$ are discharged relatively quickly. The discharging operation in this case occurs quickly enough to allow detection of the following natural, not stimulated cardiac action following a stimulation pulse. This is relatively simple since the heart in any case does not exhibit any spontaneous self-activity during the refractory time following a stimulation.

In contrast, detecting the cardiac response is considerably more difficult because the evoked potentials appear within a short time after the stimulation pulse. The response therefore can be measured only with high-capacity electrodes which, owing to their high capacity, are charged to a relatively low voltage only by a stimulation pulse, which does not interfere with the measuring of the evoked potentials following the autoshort.

The above described, automatic optimizing of the stimulation pulse amplitude therefore requires that the capacity of the pacemaker electrode 2 is sufficiently high, whereas this function should be switched to inactive if the electrode capacity is too low.

The pacemaker 1 consequently determines the capacity of the electrode system (and thus indirectly that of the pacemaker electrode 2) and switches off the automatic optimizing of the pulse intensity if the capacity drops below a predetermined minimum value.

The pacemaker 1 has a current measuring instrument 8 for this, which is arranged in the output circuit and measures the current being discharged for each stimulation pulse or special measuring pulse. The output signal from the current measuring instrument 8 is subsequently transmitted to an integrator 9, which determines from the current path the electrical charge being discharged during a stimulation pulse. A voltage measuring instrument (i,e, voltage meter) 10 is furthermore provided for measuring the voltage at the interface immediately following the end of a stimulation pulse or after or during a measuring pulse, which voltage essentially is equal to the charging voltage for the electrode capacity. A current measuring instrument is not needed in the case of a constant-current measurement (see text below for this).

A processing or evaluation unit 11 (ALU—arithmetic logical unit) has inputs connected with the outputs of integrator 9 and voltage meter 10, which unit computes the electrode capacity $C_H$ based on the formula $$C_H = \frac{Q}{U}$$

from the voltage U, measured above the electrode capacity and the discharged electrical charge.

The electrode capacity $C_H$, determined in this way, is then transmitted to the input of a comparator unit 12 where it is compared to a minimum value $C_{Min}$, present at the other input, which is necessary for detecting the evoked potentials and thus for realizing the automatic optimizing of the pulse amplitude. $C_{Min}$, is stored in a programmable comparative value memory 12a.

If the measured electrode capacity is above this minimum value, then a corresponding signal is transmitted via the comparator unit output to an input of the control circuit 7, whereupon the control circuit 7 optimizes the stimulation pulse amplitude in the above described manner.

However, if the electrode capacity $C_H$ falls below the required minimum value $C_{Min}$ then the optimizing of the pulse amplitude is blocked and the control circuit 7 adjusts the stimulation amplitude to a preset value that ensures a secure stimulation of the heart.

Figure 3A:
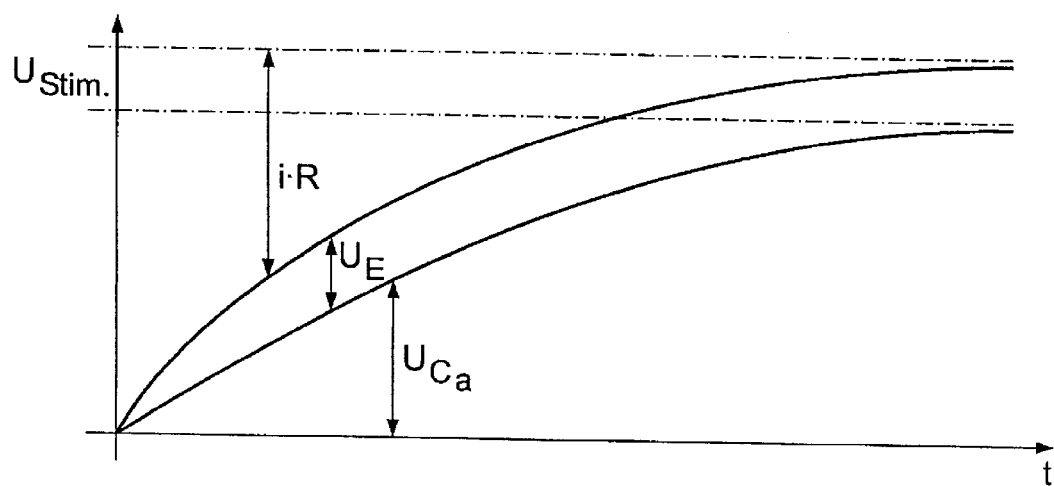
FIGS. 3a and 3b Show the voltage course at the interface or at the various components in the output circuit.

The voltage flow at the various components of the output circuit is shown in detail in FIG. 3a, wherein it is assumed that a constant voltage pulse with amplitude $U_{Stim}$ is generated before the output capacitor $C_a$. Owing to the fact that output capacitor as well as electrode capacity $C_H$ are completely discharged at the start of the stimulation pulse, the complete stimulation voltage initially drops via the ohmic resistors, arranged in the output circuit. However, the two capacities are charged during the course of the stimulation pulse, so that the current drops exponentially.

Figure 3B:
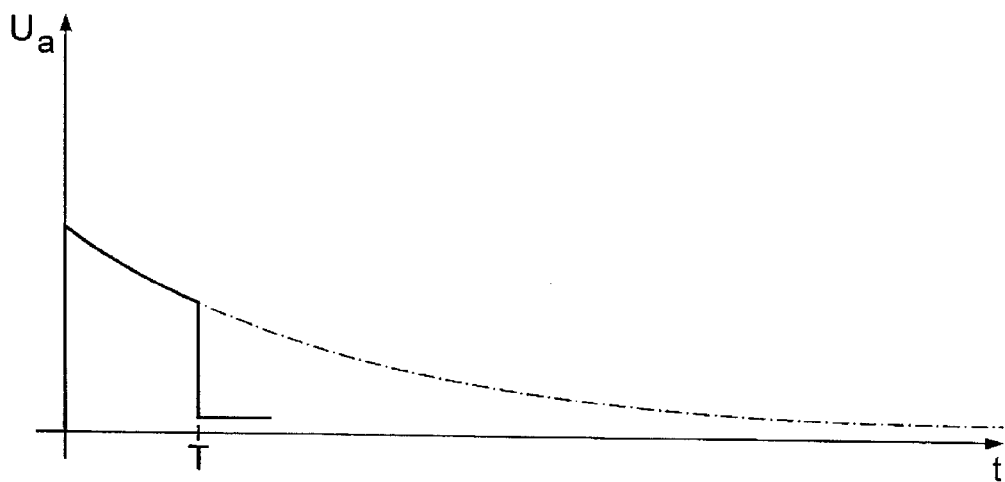

FIG. 3b shows the voltage course that can be measured at the output connection for the pacemaker electrode. In conformity with FIG. 3a, the output voltage $U_a$ at the start of the stimulation pulse corresponds to the total voltage $U_{Stim}$ since the output capacitor $C_a$ is initially discharged. However, the output capacitor is charged up during the course of the stimulation pulse, which leads to an exponential drop of the output voltage until the end of the stimulation pulse, that is at point in time t=T. At that point in time, the current in the output circuit jumps back to zero, so that the output voltage drops to the voltage level above the electrode capacity, thereby making it possible to use a simple voltage measurement to determine the electrode capacity immediately following the end of the stimulation pulse.

In this case, linear relationships exist up to artifact voltage values of approximately 0.5 V. The buildup of higher voltages should therefore be avoided in the interest of the information that can be provided by the measurements. For that reason, the direct use of standard stimulation pulses with an amplitude of several volts as measuring pulses makes sense only if electrodes with very high capacity are used. It would be better to resort to lower amplitude values, which can also be programmed into modern pacemaker circuits.

It is furthermore preferable if the voltage is not measured immediately following the end of the measuring pulse, but only after a predetermined pulse decay time of several milliseconds. Finally, it must be noted here that strictly speaking not only the voltage following the pulse, but also the voltage difference before and after the pulse must be measured at the electrode for a potential pulse measurement as well as a constant-current measurement since an offset voltage (not known without previous measurement) is superimposed on the actual artifact. FIG. 1 accordingly would have to be supplemented with a memory for measured values and a subtraction stage, connected in series after the voltage measuring instrument 10 and before the ALU 11.

The above-described measuring technique can be modified advantageously to the effect that a constant current is used. A galvanostatic control circuit is formed here in order to keep a constant current flowing through the measuring electrode, which circuit comprises—as is known per se—a current-feeding counter electrode and in principle also a current-free reference electrode, as well as a measuring current amplifier and an output amplifier. The potential present at the electrode to be measured is measured by means of a high-impedance probe in the form of a nearly load-free scanning.

In view of the very small polarization flows, a reference electrode can be omitted in practical operations when testing implantable pacemaker electrodes. Sufficiently accurate measurements are possible for bipolar systems between tip and ring and for unipolar systems between tip and pacemaker housing.

Figure 4:
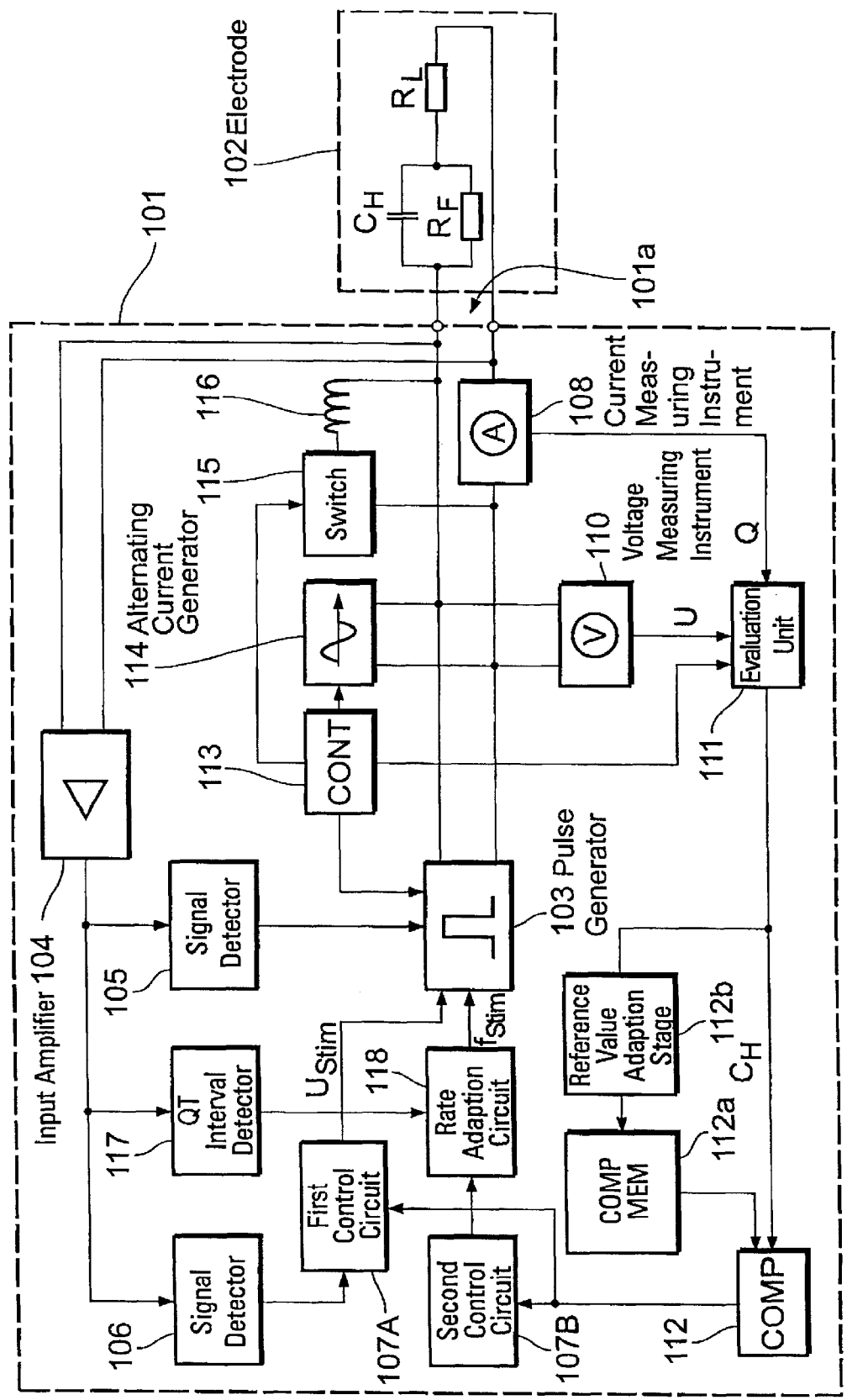
FIG. 4 Shows an operational block diagram of a pacemaker as additional exemplary embodiment.

FIG. 4 shows a pacemaker embodiment that is modified as compared to FIG. 1, again in the form of an operational block diagram. Functional components that are in principle the same are given reference numbers close to those used for FIG. 1 (e.g. the reference number 102 for the electrode essentially refers to the same function as the number 2) and are not explained again in the following.

The pacemaker sketched in FIG. 4 differs from the one shown in FIG. 1 primarily by the means for adapting the stimulation rate and a changed measuring arrangement and evaluation arrangement for testing the electrode capacity.

The rate adaptation means (known per se) comprise a QT interval detector 117, connected in series after the output of input amplifier 4, and a rate-adaptation circuit 118 that is connected to the QT interval detector output. The time interval between a stimulation pulse and a predetermined segment of the evoked cardiac signal (T-wave) is determined in the QT interval detector 117. In the rate-adaptation circuit 118, a rate-control signal is generated on the basis of the measured time interval and with the aid of a previously stored value table, which signal is then transmitted to the stimulation pulse generator 103.

In the same way as the automatic adjustment of the stimulation amplitude can be blocked as described in the above (in this case via a first control circuit 107A), the operation of the rate-adaptation circuit 118 can be blocked by way of a second control circuit 107B that is connected on the output side to the rate-adaptation circuit if the electrode capacity is too low and this results in the danger of the evoked potentials, which are detected with the electrode 102, being distorted.

In the arrangement according to FIG. 4, the testing of the electrode capacity—controlled by a test control circuit (controller) 113—is carried out during the breaks between stimulation pulses and by means of a tunable alternating current generator 114. The frequency of the alternating current generator 114 is changed gradually (preferably in the range of 0.1 Hz to 10 kHz) in accordance with a program sequence stored in the program memory for test control circuit 113. For each step, the outgoing line leading to the electrode 102 is respectively connected for a predetermined time interval via a switch 115 to a known inductance 116. As a result, respectively one resonant circuit is formed as load for the alternating current generator 114 from the inductance 116 and the electrode capacity $C_H$. A voltage and/or current measurement, carried out for each step with the aid of the current measuring instrument 108 and the voltage measuring instrument 110, makes it possible to determine an oscillating frequency for the oscillating circuit and thus the capacity $C_H$ in an evaluation unit 111.

A final, special feature of the arrangement according to FIG. 4 provides for a reference value adaptation stage 112b, which supplies a minimum value, determined as sliding mean value of the electrode capacities measured over a predetermined period of time, to the comparative memory 112a. As a result, long-term fluctuations of the electrode capacity do not effect the control or blocking functions of the control circuits 107A, 107B.

The invention in its embodiments is not limited to the aforementioned, preferred exemplary embodiments. Rather, a number of variants are conceivable which make use of the illustrated solution, even if the embodiments are designed differently.

Thus, in a further modification of the measuring principle, the electrode capacity can also be determined via a time measurement, that is to say by detecting the point in time after a constant-current pulse is transmitted to the electrode at which a specified voltage appears on the electrode, e.g. a voltage of 300 mV.

A shut-down (blocking) of the processing of signals, which are picked up via the pacemaker electrode and may be distorted if the electrode capacity is too low, or of the functions based on this evaluation is conceivable, not only in connection with the automatic adjustment of the stimulation amplitude or the rate adaptation—as described in the above—but also in other connections.

What is claimed is:

1. An electrostimulator comprising:

one heart-working electrode adapted to be implanted in tissue adjacent to a heart;

an output connection for connection to the one working electrode;

a test signal generator having an output connected to the output connection for generating one of a pulse-shaped and periodically changeable test signal and feeding the signal to the output connection for stimulating the heart;

a first measuring device having an input connected to the output connection for measuring at least one of an electrical voltage present at the output connection and a current flowing over the output connection; and an evaluation device having an input connected at least indirectly to the first measuring device for generating an output signal that reflects the working electrode capacity in dependence on at least one of the current and voltage present at the output connection and for determining whether the heart has been stimulated.

2. The electrostimulator according to claim 1, wherein the test signal generator produces the test signal that has an amplitude considerably below an amplitude of a stimulation pulse required to generate electrical pulses.

3. The electrostimulator according to claim 1, further comprising a measuring electrode, wherein the first measuring device comprises a voltage measuring instrument switched parallel to the test signal generator and further comprising a galvanostatic automatic control circuit coupled to the test signal generator to keep a constant current flowing through the measuring electrode.

4. The electrostimulator according to claim 1, further comprising an impedance spectrogram; and an inductance coupled to the output connection and cooperating with the working electrode to form an oscillating circuit, wherein the test signal generator comprises an oscillator and the evaluation device comprises means for determining the oscillating frequency of the one of the oscillating circuit or of the impedance spectrogram.

5. The electrostimulator according to claim 4, and further comprising a switching device linking the inductance to the output connection.

6. The electrostimulator according to claim 4, wherein the test signal generator comprises a tunable oscillator.

7. The electrostimulator according to claim 1, wherein the working electrode comprises an endocardially arranged pacemaker electrode and the electrostimulator comprises a pacemaker connectable to the pacemaker electrode.

8. The electrostimulator according to claim 7, wherein the test signal generator operable with a lower pulse amplitude for the measuring of signals is a stimulation pulse generator.

9. The electrostimulator according to claim 8, wherein the stimulation pulse generator has a pacemaker function and a pacemaker parameter; and wherein the electrostimulator further comprises an input amplifier connected to the output connection for amplifying signals received from the pacemaker electrode; a signal detector connected in series after the input amplifier for detecting a cardiac response in the signal and for generating a first control signal in reaction to a missing response following a stimulation pulse; a control circuit having an input connected to the signal detector for performing a first control operation with respect to one of the pacemaker function and the pacemaker parameter upon the appearance of the first control signal, and performing a second control operation if the first control signal does not appear.

10. The electrostimulator according to claim 9, where in the evaluation device includes comparator unit for comparing the output signal that reflects the electrode capacity to a comparison value, which comparator unit generates a second control signal if the comparison value is exceeded, and wherein the control circuit has a control input connected to the output of the comparator unit for performing the first or second control operation only if the second control signal is present at the control input.

11. The electrostimulator according to claim 9, wherein the control circuit has an output connected with the stimulation pulse generator of the pacemaker and is adapted for increasing at least one of the amplitude and the duration of the stimulation pulses following the appearance of the first control signal and for reducing these if the first control signal does not appear.

12. The electrostimulator according to claim 9, further comprising a device for adapting a stimulation rate in reaction to the pacemaker electrode signal, and which permits or blocks a rate adaptation in dependence on at least one of the first and second control signal, and wherein said control circuit is connected to a control input of the device for adapting the stimulation rate.

13. The electrostimulator according to claim 9, and further comprising a comparison value memory for storing a comparison value and having an output coupled to the comparison unit.

14. The electrostimulator according to claim 13, wherein the comparison value memory is programmable.

15. The electrostimulator according to claim 13, wherein the comparison value memory stores a predetermined comparison value.

16. The electrostimulator according to claim 13, wherein the comparison value memory has an input coupled to the output of the evaluation device and stores a comparison value obtained during preceding evaluations by the evaluation device.

17. An electrostimulator comprising:

one heart-working electrode adapted to be implanted in tissue adjacent to a heart;

an output connection for connection to the one working electrode;

a test signal generator having an output connected to the output connection for generating one of a pulse-shaped and periodically changeable test signal and feeding the signal to the output connection for stimulating the heart;

a first measuring device includes a voltage measuring instrument parallel connected to the test signal generator and having an input connected to the output connection for measuring an electrical voltage present at the output connection;

a second measuring device comprising a current measuring instrument, connected in series with the test signal generator and the output connection, for measuring the current flowing over the output connection when the test signal is flowing through the connection; and an evaluation device having an input coupled to the first and second measuring devices for generating an output signal that reflects the working electrode capacitance in dependence on at least one of the current and voltage present at the output connection to determine whether the heart has been stimulated.

18. The electrostimulator according to claim 17, further comprising an integrator connected in series after the current measuring instrument and having an output connected to the evaluation device for determining an electrical charge that is discharged during the test signal.

19. A method of using the electrostimulator according to claim 3, wherein the constant current flowing through the measuring electrode is pulse-shaped, said method comprising:

measuring and storing first, second and third potential values and the length of the constant-current pulse at the working electrode immediately before and after the start of the constant-current pulse and immediately before switching off the constant-current pulse;

determining a series resistance of the measuring electrode by dividing the potential difference from the first and the second potential values by the constant current value, and determining a phase-limit capacity of the working electrode from the third and second potential values by forming a quotient of the product of pulse length and pulse value of the constant current and the potential difference.

20. The method according to claim 19, wherein the constant-current pulse consists of a double pulse with mutually inverse current direction for the two partial pulses, the method further including:

determining the potential differences, the pulse lengths, the series resistances and the phase-limit capacities of the measuring electrode separately for each current direction; and subsequently determining the average values for the series resistance and the phase-limit capacity.

* * * * *